US009239456B2

(12) United States Patent
Foelling

(10) Patent No.: US 9,239,456 B2
(45) Date of Patent: Jan. 19, 2016

(54) WIDEFIELD MICROSCOPE ILLUMINATION SYSTEM AND WIDEFIELD ILLUMINATION METHOD

(75) Inventor: Jonas Foelling, Heidelberg (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 170 days.

(21) Appl. No.: 14/111,759

(22) PCT Filed: Apr. 11, 2012

(86) PCT No.: PCT/EP2012/056579
§ 371 (c)(1),
(2), (4) Date: Nov. 20, 2013

(87) PCT Pub. No.: WO2012/140083
PCT Pub. Date: Oct. 18, 2012

(65) Prior Publication Data
US 2014/0061445 A1   Mar. 6, 2014

(30) Foreign Application Priority Data

Apr. 15, 2011   (DE) .......................... 10 2011 017 078

(51) Int. Cl.
*G02B 21/06* (2006.01)
*G02B 21/08* (2006.01)
(Continued)

(52) U.S. Cl.
CPC .............. *G02B 21/06* (2013.01); *G02B 21/088* (2013.01); *G02B 21/125* (2013.01); *G02B 21/16* (2013.01); *G01N 21/6458* (2013.01); *G02B 21/367* (2013.01)

(58) Field of Classification Search
CPC .... G02B 21/06; G02B 21/088; G02B 21/125; G02B 21/16; G02B 21/367; G01N 21/6458
USPC .................. 359/385, 387–389; 250/214.1
See application file for complete search history.

(56) References Cited

U.S. PATENT DOCUMENTS

2002/0186463 A1\*  12/2002  Hoppen ..................... 359/368
2003/0021035 A1   1/2003  Kusaka
(Continued)

FOREIGN PATENT DOCUMENTS

DE   10 2006 028 530   5/2007
DE   10 2006 021 317   10/2007
(Continued)

OTHER PUBLICATIONS

English translation of the Written Opinion of the International Search Authority for PCT/EP2012/056579.
(Continued)

*Primary Examiner* — Frank Font
(74) *Attorney, Agent, or Firm* — Alexander R. Schlee; Schlee IP International, P.C.

(57) ABSTRACT

A widefield microscope illumination system and a method for illumination, the system having a microscope objective with an optical objective axis, an illumination light source sending widefield illumination light along illumination beam paths having corresponding illumination axes along which the illumination light penetrates into the microscope objective through illumination light entry sites located within a predetermined illumination light entry area, a spatially resolving light detector detecting detected light sent from an illuminated sample through the microscope objective along a detected light beam path, and an automatic illumination light beam path manipulation device, controlled by a control system, which is arranged in front of the microscope objective in relation to the direction of the illumination light beam path, and by which illumination light beam path manipulation device the illumination axes are automatically movable at time intervals to a plurality of illumination light entry sites.

13 Claims, 4 Drawing Sheets

(51) Int. Cl.
  *G02B 21/12* (2006.01)
  *G02B 21/16* (2006.01)
  *G01N 21/64* (2006.01)
  *G02B 21/36* (2006.01)

(56) References Cited

U.S. PATENT DOCUMENTS

| | | |
|---|---|---|
| 2006/0250689 A1 | 11/2006 | Ulrich et al. |
| 2007/0153373 A1 | 7/2007 | Uhl |
| 2009/0046298 A1* | 2/2009 | Betzig ............... G01N 21/6445 356/521 |
| 2009/0134342 A1 | 5/2009 | Hell et al. |
| 2011/0036996 A1* | 2/2011 | Wolleschensky .. G01N 21/6458 250/459.1 |
| 2011/0109736 A1* | 5/2011 | Mertz et al. ..................... 348/79 |
| 2011/0160083 A1 | 6/2011 | Hell et al. |
| 2011/0226965 A1 | 9/2011 | Wolleschensky et al. |
| 2012/0140057 A1 | 6/2012 | Borck et al. |

FOREIGN PATENT DOCUMENTS

| | | |
|---|---|---|
| DE | 10 2006 033 306 | 1/2008 |
| DE | 10 2008 024 568 | 12/2009 |
| DE | 10 2008 059 328 | 6/2010 |
| DE | 10 2009 037 366 | 2/2011 |
| EP | 1 697 781 | 9/2006 |
| EP | 1 857 853 | 11/2007 |
| WO | 2005031429 | 4/2005 |
| WO | 2006127692 | 11/2006 |
| WO | 2007128434 | 11/2007 |
| WO | 2009149178 | 12/2009 |

OTHER PUBLICATIONS

Resolution of $\lambda/10$ in Fluorescence Microscopy Using Fast Single Molecule Photo-Switching, Geisler et al., Appl. Phys. A 88, 223-226 (2007).

Sub-Diffraction-Limit Imaging by Stochastic Optical Reconstruction Microscopy (STORM), Rust et al., Nature Methods, vol. 3 No. 10, Oct. 2006.

English translation of International Search Report for PCT/EP2012/056579 dated Jul. 13, 2012.

* cited by examiner

WIDEFIELD MICROSCOPE ILLUMINATION SYSTEM AND WIDEFIELD ILLUMINATION METHOD

CROSS-REFERENCE TO RELATED APPLICATIONS

This application is a national phase of the International Application PCT/EP2012/056579 filed Apr. 11, 2012 that claims priority from the German patent application DE 10 2011 017 078.2 filed on Apr. 15, 2011. The content of these aforementioned documents is herewith incorporated by reference.

TECHNICAL FIELD OF THE INVENTION

The invention relates to a widefield microscope illumination system having a microscope objective that comprises an optical objective axis, the illumination light being sent through the objective onto a sample viewed with a microscope; and to a corresponding illumination method.

BACKGROUND OF THE INVENTION

In the recent past, light-microscopy methods have been developed with which, based on a sequential, stochastic localization of individual point-like objects (in particular, fluorescent molecules), it is possible to display image structures that are smaller than the diffraction-related resolution limit of classic light microscopes. Such methods are described, for example, in WO 2006/127692 A2; DE 10 2006 021 317 B3; WO 2007/128434 A1, US 2009/0134342 A1; DE 10 2008 024 568 A1; "Sub-diffraction-limit imaging by stochastic optical reconstruction microscopy (STORM)," Nature Methods 3, 793-796 (2006), M. J. Rust, M. Bates, X. Zhuang; "Resolution of Lambda/10 in fluorescence microscopy using fast single molecule photo-switching," Geisler C. et al., Appl. Phys. A, 88, 223-226 (2007). This new branch of microscopy is also referred to as "localization microscopy."

The new methods have in common the fact that the structures to be imaged are prepared with markers that possess two distinguishable states, namely a "bright" state and a "dark" state. If fluorescent dyes are used as markers, for example, the bright state is then a fluorescence-capable state and the dark state is a non-fluorescence-capable state. In order for sample structures to be imaged at a resolution that is smaller than the classic resolution limit of the image-producing optical system, a small subset of the markers is then repeatedly prepared into the bright state. This subset is referred to hereinafter as an "active subset." The active subset must be selected so that the average spacing between adjacent markers in the bright state—and thus the state capable of imaging by light microscopy—is greater than the resolution limit of the imaging optical system. The luminance signals of the active subset are imaged onto a spatially resolving light detector, e.g. a CCD camera. A spot of light, whose size is determined by the resolution limit of the image-producing optical system, is thus acquired from each marker.

The result is that a plurality of individual raw-data images are acquired, in each of which a different active subset is imaged. In an image analysis process, the center points of the light distributions (representing the markers that are in the bright state) are then determined in each individual raw-data image. The center points of the light spots identified from the individual raw-data images are then combined into one overall depiction. The high-resolution overall image produced by this overall depiction reflects the distribution of the markers.

For representative reproduction of the structure to be imaged, a sufficient number of signals must be detected. But because the number of markers in the particular active subset is limited by the minimum average spacing that must exist between two markers in the bright state, a very large number of individual raw-data images must be acquired in order to image the structure completely. The number of individual raw-data images is typically in a range from 10,000 to 100,000.

The time required for acquiring an individual raw-data image is limited at the low end by the maximum image acquisition rate of the imaging detector. This leads to comparatively long total acquisition times for a sequence of individual raw-data images that is necessary for the overall depiction. The total acquisition time can thus amount to as much as several hours.

In order to reduce the total acquisition time as much as possible and to keep it as short as possible, the acquisition time of each individual raw-data image must be minimized. This requires that the individual light spots that generate the markers be produced very quickly, although of course they must nevertheless be bright for the purpose of good localization. This means that when they are in the active state, the markers must emit a very large number of photons very quickly before they transition back into the inactive state. If the acquisition time of the individual raw-data image is then adapted in accordance with the average luminous time of the markers, the result is the fastest possible image acquisition. Typical markers are (switchable or non-switchable) fluorescing molecules. The more photons of excitation light they acquire, the more photons they emit within a certain time period. It is therefore necessary to irradiate the molecules with high light intensities, this being the only way to enable maximally fast image acquisition.

High light intensities are advantageous in particular when quite ordinary, non-switchable fluorescent molecules are used as markers. These have the advantage, as compared with special switchable dyes, of generally being much easier to handle and yielding better color results. In addition, a large number of different dyes are available. The number of special switchable dyes is limited, and often they are not easy to handle. The active state of these standard dyes thus corresponds to the molecule in its ground state or first excited state, in any event with the capability of emitting photons. The inactive state is a dark state of the molecule as exhibited by every ordinary fluorescent molecule, for example a triplet state or a reduced or oxidized state. The molecule can typically change with a low probability from the excited state into the dark state, and after a certain time will automatically transition back into the ground state in which it can fluoresce again. Because of this fact, the molecule exhibits blinking behavior: it emits photons until it spontaneously transitions out of the excited state into the dark state. The entirety of these photons forms a light spot. The molecule then remains in the dark state until it transitions spontaneously back into the active state. During the dark-state time the molecule emits no photons and thus no detectable signal. Because the dark state can be very long-lived, but because at high light intensity the light spots occur very quickly, this behavior manifests itself as blinking. In order to achieve, in these circumstances, a state in which only individual molecules are visible (i.e. are in the active state), the light intensity of the excitation light must be very high. Only in this way is it possible for almost all the molecules to be in the inactive state, since as soon as they spontaneously change into the active state they emit (because of the high intensity of the excitation light) a rapid sequence of photons and then disappear again "in a flash." Only a very few molecules are therefore visible simultaneously. The high intensity of the excitation light here therefore not only makes possible rapid image acquisition, but is also useful for establishing a sufficiently low ratio of active to inactive markers.

It has become apparent from the explanations above that a high level of light output must be introduced into the sample. The sample is usually illuminated using the so-called "widefield" method. This means that a large area in the sample is illuminated as homogeneously as possible, specifically exactly that region which is imaged by the imaging optics onto the detector. Illumination typically occurs through the same objective that also collects the fluorescent light and images the sample onto the detector by means of a corresponding further optic.

In order to allow a large region of the sample to be illuminated as homogeneously as possible, light is focused into the rear focal plane of the objective. Depending on the size of the focus in the rear focal plane, what results in the front focal plane, i.e. in the sample plane, is the size of the illuminated field. The smaller the focus in the rear focal plane, the larger the illuminated field, and vice versa. In order to allow a correspondingly large region to be illuminated, all of the excitation light is therefore directed as a small light beam into the objective. The consequence of this is that in typical objectives, the excitation light passes through the lens elements in the objective as a relatively narrow ray bundle. There are regions in the objective in which the ray bundle is wider or narrower. In general, however, with this type of illumination the entire aperture of the lens elements is typically not even utilized, but instead the light always passes through the lens elements only in a very thin ray bundle. Since it is generally necessary, as already mentioned above, to introduce very high light power levels into the sample, extremely high light intensities are achieved as a result of the thin ray bundle in the objective. Laser light is therefore often used for widefield illumination in localization microscopes in order to achieve these light intensities.

More-complicated lens elements or lens systems, such as those that occur in objectives, typically contain various materials that can experience damage at high light intensities. The "weakest link" here is typically the optical cement with which, for example, different lens parts are joined to one another. In extreme cases, however, even surface layers on the lens elements, or the elements themselves, can be damaged.

As the "load" on the optic due to the strong illumination increases, the optic can thus suffer damage that can have a disadvantageous effect on the beam path of the illumination and on detection. "Blind spots" can occur, for example, producing point-like absorption, diffraction, or severe scattering of light. Holes in the elements, etc. are also conceivable. Such damage can make an objective completely unusable. For example, if a blind spot develops exactly in the illumination beam path (where it would preferentially develop as a result of the beam load), the objective would no longer be usable, since light (or at least a "clean" illumination beam) would no longer be able to emerge from the objective toward the sample. Damage of this kind would also have a negative effect on the detection beam path, since it too passes through the objective, and the detected light would be influenced (e.g. scattered) at the damaged sites in the objective.

Although it is known to manufacture simple optical systems without cement, these systems typically are mechanically more susceptible and less stable, and disadvantages are also conceivable in terms of other optical properties. These systems are appreciably more stable in terms of beam load, however, since the optical cement that is susceptible to beam load is omitted. With complicated optical systems such as special objectives, however, production without optical cement is not possible by present-day industrial standards, or is possible only with considerable extra outlay. It is thus extremely important to prevent such damage even in the context of cemented optical systems, since otherwise the service life of the objectives for practical use is greatly limited, the more so since objectives are very complex—and correspondingly expensive—components.

What emerges upon closer examination of the problem is that typical radiation damage proceeds according to a similar pattern. In most cases the damage does not occur immediately when the light is first switched on. The light power levels used are often ones that the problematic optical components can withstand for an extended time. A slow decrease in the transmittance of the optical system can nevertheless often be observed. In the case of cemented optics this is presumably attributable to a change in the cement under the influence of light. After a certain time a critical threshold is reached, however, and the questionable component exhibits a sudden change (in fractions of a second) at the illuminated site; the result of this can be that at the illuminated site and in its vicinity, the component can no longer transmit light at that point or (if the reaction is correspondingly severe) in its entirety, or it may exhibit severe light scattering and has thus become unusable.

Before this sudden change occurs, what is detectable is at most a marginal change in optical properties, which may be measurable with suitable and exact measurement methods but is usually negligible. The optic is thus usable in entirely normal fashion until the change suddenly occurs. The damage to or destruction of the objective is therefore a highly nonlinear process, and this is exploited in the invention below.

It is understood that the problem occurs not only with localization microscopes but also with any type of microscope that uses a high illumination light intensity which is sent through the objective. Although this is particularly relevant to fluorescence microscopes, it can also be the case with light microscopes.

SUMMARY OF THE INVENTION

It is an object of the invention to prevent, in the context of a widefield illumination that is accomplished using a microscope objective, damage to the objective even in a context of high illumination light intensity.

According to a first aspect of the invention, this is achieved by a widefield microscope illumination system having: a microscope objective that comprises an optical objective axis; an illumination light source that sends widefield illumination light along illumination beam paths having corresponding illumination axes along which the illumination light penetrates into the microscope objective through illumination light entry sites located within a predetermined illumination light entry area; a spatially resolving light detector that detects detected light sent from an illuminated sample through the microscope objective along a detected light beam path; and an automatic illumination light beam path manipulation device, controlled by a control system, which is arranged in front of the microscope objective in relation to the direction of the illumination light beam path, and by means of which illumination light beam path manipulation device the illumination axes is are automatically movable at time intervals to a plurality of illumination light entry sites.

According to a second aspect of the invention, this is achieved by means of a widefield illumination method for illuminating samples viewed with a microscope, the microscope being equipped with: a microscope objective that comprises an optical objective axis; and an illumination light source that sends widefield illumination light along illumination beam paths having corresponding illumination axes along which the illumination light penetrates into the microscope objective through illumination light entry sites located within a predetermined illumination light entry area; the illumination method being equipped with repeated, automatic, parallel adjustment of the illumination axis relative to the optical objective axis at time intervals, in such a way that a lateral offset of the illumination axis relative to the objective axis is automatically adjusted, so that the illumination light entry site is adjusted within the predetermined illumination light entry area at time intervals such that the objective is protected from damage by illumination light.

DETAILED DESCRIPTION OF THE INVENTION

According to a preferred embodiment of the invention, the illumination axes always extend parallel to the objective axis. Although slightly deviating angles of entry into the specimen result in a lateral offset of the illumination with respect to the specimen, this either can be ignored or, for certain special applications, can in fact be desired. As a rule, however, the entry angle will be selected to be at least substantially parallel to the objective axis, at least when compensation for a greater lateral offset, relative to the sample, of the illumination light emerging from the objective is to be avoided. Expressed in method steps, the preferred embodiment contains the steps of parallel orientation of the illumination axes relative to the objective axis, and maintenance of that parallelism upon automatic adjustment of the lateral offset of the illumination axis relative to the objective axis.

According to a preferred embodiment of the invention, the widefield microscope illumination system is a constituent of a localization microscope. This particular application results from the fact that relatively high light intensities are sent through the objective as illumination light, and only a relatively small part of the aperture of the objective is utilized for entry of the illumination light beam into the objective, i.e. the beam cross section is relatively small as compared with the overall entry area of the objective and in some circumstances (but not obligatorily) becomes collimated to a larger beam cross section only upon passage through the objective. It is also applicable, however, to microscopes other than localization microscopes, for example to light microscopes, if high light intensities are used therein for the illumination light.

According to a preferred embodiment of the invention, the microscope illumination system is a constituent of a TIRF illumination system. This is advantageous in particular because with the illumination system according to the present invention, different illumination angles in the objective plane can be established by relatively simple implementation of a lateral offset of the illumination light relative to the optical objective axis. According to an advantageous refinement of the invention, the method according to the present invention is accordingly notable for the fact that a selection of the predefined illumination light entry area is made from at least two different illumination light entry areas that are associated with different illumination modes, which advantageously can be epifluorescence illumination and TIRF illumination. Epifluorescence illumination can also be effected using angles deviating slightly from the optical axis, although this deviation can be ignored for illumination of the sample. Although it is possible in practice to work with far smaller deviations, even a deviation of 30 degrees from the optical objective axis would be negligible for many applications for the purpose of illuminating the sample.

According to a preferred embodiment of the invention, the illumination light beam path manipulation device comprises an optomechanical system, acousto-optical modulators (AOMs), or electro-optical modulators (EOMs), which establish an adjustable beam offset and thus an illumination light entry site that is adjustable with respect to the optical objective axis. AOMs and EOMs in particular offer the possibility of very quickly bringing about a lateral offset of the illumination light beam path. But because the objectives can already withstand the beam load over a certain period of time, an optomechanical system is also sufficient in terms of switchover speed.

According to a preferred embodiment of the invention, the control system comprises a random generator that controls a permitted adjustable beam offset in the region of the predetermined illumination light entry area for the illumination light into the objective, all the illumination light entry sites permitted by the control system being located within this predetermined illumination light entry area. Expressed in terms of the method according to the present invention, what occurs advantageously is a random selection of the respective illumination light entry sites of the illumination light within the predefined illumination light entry area, and maintenance of those respective illumination light entry sites over the respective time intervals until the respective next illumination light entry site within the predefined illumination light entry sites is randomly selected. As an alternative, different illumination light entry sites can be traveled to according to a predefined pattern, i.e. by selection of the respective illumination light entry sites of the illumination light within the predefined illumination light entry area according to a predefined pattern, and maintenance of those respective illumination light entry sites over the respective time intervals until the respective next illumination light entry site is selected within the predefined illumination light entry sites according to the predefined pattern.

According to a preferred embodiment of the invention, the illumination light entry sites that have already been traveled to, and the quantity of radiation sent thereonto, are stored. This on the one hand allows the user to deduce when the objective will probably be destroyed, so that it can be replaced preventively. In addition, by means of this information the automatic illumination light adjusting device can always, upon a change in the illumination light penetration sites, select the new illumination light penetration site in such a way that it falls into a region that has so far experienced less damage as compared with other sites. This allows a more uniform, and thus service-life-lengthening, effect to be achieved than in the case of an entirely randomly controlled adjustment.

According to a preferred embodiment of the invention, a control interface is provided by means of which a control instruction adjusting the predetermined illumination light entry area can be entered. This can be done either in order to establish a different illumination mode that accompanies a different predetermined illumination entry area, or in order to find further alternatives in order to reduce stress on the objective, for example a site located farther away from the optical axis if the sites close to the optical objective axis have been, so to speak, used up by an excessive beam load.

According to a preferred embodiment of the invention, the predetermined illumination light entry area is a circular, circular-segment-shaped, annular, or annular-segment-shaped area. Any other desired areas can, however, of course also be selected, for example square, rectangular, or triangular.

According to a preferred embodiment of the invention, a measurement device is provided which monitors the transmittance of the objective and sends a control signal to the control system when the transmittance falls below a predetermined threshold value. In other words, a measurement of the optical transmittance of the objective is performed for the respective illumination light entry sites, and the time intervals are adjusted in accordance with a change over time in optical transmittance for the respective illumination light entry site. A consequence of this is that an adjustment of the illumination light entry area into the objective does not occur until the previous site has been, so to speak, used up. The number of switchover operations can thus be limited. Since these disruptions are, however, minimal and usually are not even noticed, the switchover can also occur at predetermined time intervals or at time intervals that can be set by a control signal.

The invention will be described below in more detail:

If the illumination beam path is automatically guided, after a certain illumination time that is nevertheless below the destruction threshold of the optic, to a site in the optic located nearby, destruction of the optic at the first site can be averted. The new site can then be illuminated again for a corresponding time before the illumination beam path is shifted again to a different site. The previously illuminated sites are thus, as described above, damaged only in an optically negligible fashion. Depending on the diameter of the light beam and the size of the region of the optic on which the light beam can be displaced without causing undesired effects farther along the beam path, a very large number of different sites in the optic can be illuminated until shortly before the destruction threshold. The number of possible sites that can be illuminated determines the factor by which the lifetime of the objective can be extended.

As already indicated in the paragraph above, it is usually not possible to displace the beam path in the optic in an arbitrary manner, since this results in a change in the beam path in the following region. For very small beam diameters and a corresponding size of the optic in question, however, sufficient leeway often exists that many different positions can be traveled to, and the lifetime of the optic can thus be increased by a large multiple. This is illustrated using the concrete example of large-area illumination of a microscopic sample. The critical component in this case is the objective. A number of typical illumination modes exist, for example epifluorescence illumination. Here the excitation light is focused into the center of the rear focal plane. The consequence of this is that the light emerges in collimated fashion from the center of the objective and illuminates a large region in the sample. If the illumination beam path is then slightly offset, the light emerges from the objective at a specific angle. The farther the beam is moved away from the center of the objective aperture, the larger that angle becomes.

In practice, however, it is entirely irrelevant for many samples whether they are transilluminated by a vertical or a slightly oblique beam. This is because samples are often very flat (e.g. cells on coverslips), so that a certain angle plays no part at all. If light strikes the sample at an angle deviating slightly from the vertical, i.e. from the orientation of the optical objective axis, the sample will be illuminated almost identically as compared with vertical illumination, even though another site in the objective itself is being irradiated. Especially in the microscopy technique described above, most of the samples being worked with are flat, since thicker samples would in any case cause the problem of obtaining an undesired background signal. Numerous possible alternative illumination beam paths are thus available, making possible a multiplication of the objective service life. For all beam paths that are incident into the objective inside the ring, the deflection of the beam in the sample is negligible. All of them, however, take different paths within the objective.

TIRF illumination is another type of illumination that is likewise very popular for the microscopy technique described above. Here the illumination beam path is passed along the edge of the objective aperture. The exit angle at the objective is now so large that, with suitable samples, total reflection occurs and the sample is illuminated only by the evanescent field. Background light can thus be blocked out. The penetration depth of the evanescent light depends on the angle. The resulting exit angle is the same, however, for all points that lie on a circle having a specific radius around the center of the aperture. Numerous points on that circle can thus be traveled to without changing the penetration depth into the sample. A further effect is additionally useful here: the TIRF effect is also highly nonlinear. In other words, the onset of total reflection, and thus of the TIRF effect, is sudden, and the change in penetration depth with a change in angle is then comparatively small and, for many applications, not of primary importance. What is important principally is that a TIRF effect be achieved at all. Whether the penetration depth is then 90 nm or 200 nm is secondary for many applications. Depending on the importance of a specific penetration depth, regions having a smaller or larger radius can thus also be traveled to, and a TIRF effect is still maintained. Many further sites in the objective, offering alternative beam paths, are thus available.

It may be gathered from the explanations above that the methodology described, specifically in the exemplifying application, allows a drastic increase in the lifetime of an objective to be achieved without perceptibly limiting the functionality of the microscope.

In the applications described, specifically in widefield microscopy with epifluorescence illumination or TIRF illumination, an optical system, acousto-optical system, or optomechanical system is generally already provided, allowing the illumination beam to be manipulated in terms of the exit angles required for a TIRF effect or for epifluorescence illumination. This optomechanical system can then also be used to achieve small beam offset widths that achieve the above-described effect. The beam offset can also be effected in accordance with different patterns; for example, the beam can automatically and repeatedly travel to different points on the objective, at suitable time intervals, according to a previously defined pattern. An approach strategy controlled by a random generator can also, for example, be followed, so that a different random point in the objective is illuminated, for example, at each measurement or at another suitable point in time. Uniform beam load on the objective over a long period of time is thus achieved. The points traveled to should be located in a region that is still tolerable in terms of the undesired optical deviation from the ideal case.

The suitable point in time for traveling to a new point can be defined in various ways. On the one hand the position can be changed after relatively short time periods, but each position can be traveled to repeatedly over the lifetime of the objective. The objective is thus uniformly irradiated when considered over a longer time period, this being desirable.

On the other hand, each position can also be illuminated until shortly before the destructive radiation dose is reached, and another position can then be traveled to. The point in time at which the destructive radiation dose is reached can be ascertained in various ways; for example, test measurements can ascertain the usual dose. Each point can then correspondingly be illuminated well below the destruction threshold, so that the objective does not sustain damage sooner than necessary.

As another alternative, the fact that the destruction threshold has been reached can also be ascertained by measurements during irradiation. As already mentioned, the change in the optical system under the influence of radiation can be determined with sufficiently accurate measurement devices, for example by the fact that the transmittance of the optical system decreases slightly at single points. That transmittance can be monitored during the measurements, and below a specific limit transmittance (which is just below the destruction threshold) the illumination point can then be switched.

BRIEF DESCRIPTION OF THE DRAWINGS

The invention will be explained in more detail below in terms of preferred exemplifying embodiments of the invention with reference to the drawings, in which.

DETAILED DESCRIPTION OF THE DRAWINGS

Figure 1:
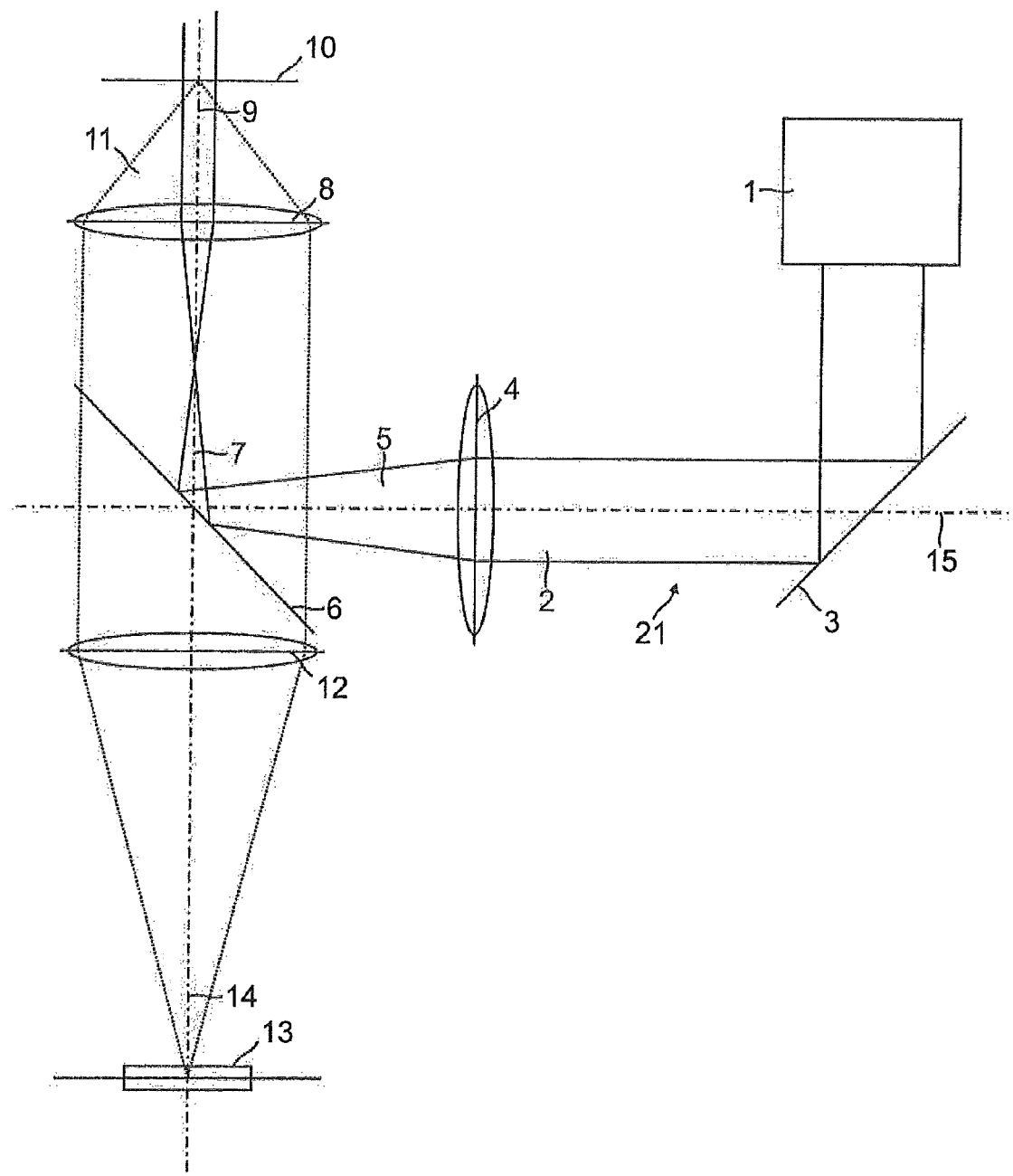
FIG. 1 schematically depicts a microscope according to the present invention with no lateral offset of the illumination light beam path relative to the optical axis of the objective.

FIG. 1 schematically shows a microscope into which the widefield microscope illumination system according to the present invention is incorporated as a constituent. For the purpose of clearer depiction, the schematic depiction departs relatively far from actual scales. The fundamental construction of the microscope as shown is that of an inverted microscope, in which the sample is located at the top and the illumination beam is sent upward from below in order to strike and illuminate the sample at the top. It is understood that a conventional construction, with a sample located at the bottom and detector at the top, can also be used. A light source 1, for example a laser, sends a first ray bundle 2 into an illumination light beam path manipulation device 21, made up for example of a tiltable mirror 3 and a lens element 4. Ray bundle 5 emerging from illumination light beam path manipulation device 21 is reflected at a dichroic mirror 6, in the form of a converging ray bundle 7, to objective 8, which is depicted here for the sake of simplicity as a single lens element. Objective 8 collimates the ray bundle and sends it, as a collimated ray bundle 9, into object plane 9. From here the detected light 11 to be detected is emitted from the specimen (not depicted here). All that is depicted here, by way of example, is detected light 11 proceeding from one point of the specimen. The specimen can of course also emit light at all other illuminated points. The light to be detected passes through objective 8 and through dichroic mirror 6 that is transparent in the direction of the detected beam path, and is directed by a tube lens 12 onto a detector 13 that permits a location allocation for the received light intensities. Examples of such location-allocating detectors are CCD cameras or CMOS cameras. As is evident from what is depicted in FIG. 1, objective 8 in conjunction with tube lens 12 focuses the detected light onto detector 13.

An optical objective axis 14 and an additional axis of symmetry 15 of illumination light manipulation device 21 are depicted with dot-dash lines. According to the depiction in FIG. 1, a lateral offset for the illumination light beam path has not been established by illumination light beam path manipulation device 21, i.e. the illumination light beam path is being sent along optical objective axis 14 into objective 8; in other words, the axis of symmetry of the illumination light beam path coincides with optical objective axis 14. This is the special case of epifluorescence illumination, in which the illumination light is usually sent centrally through objective 8.

Figure 2:
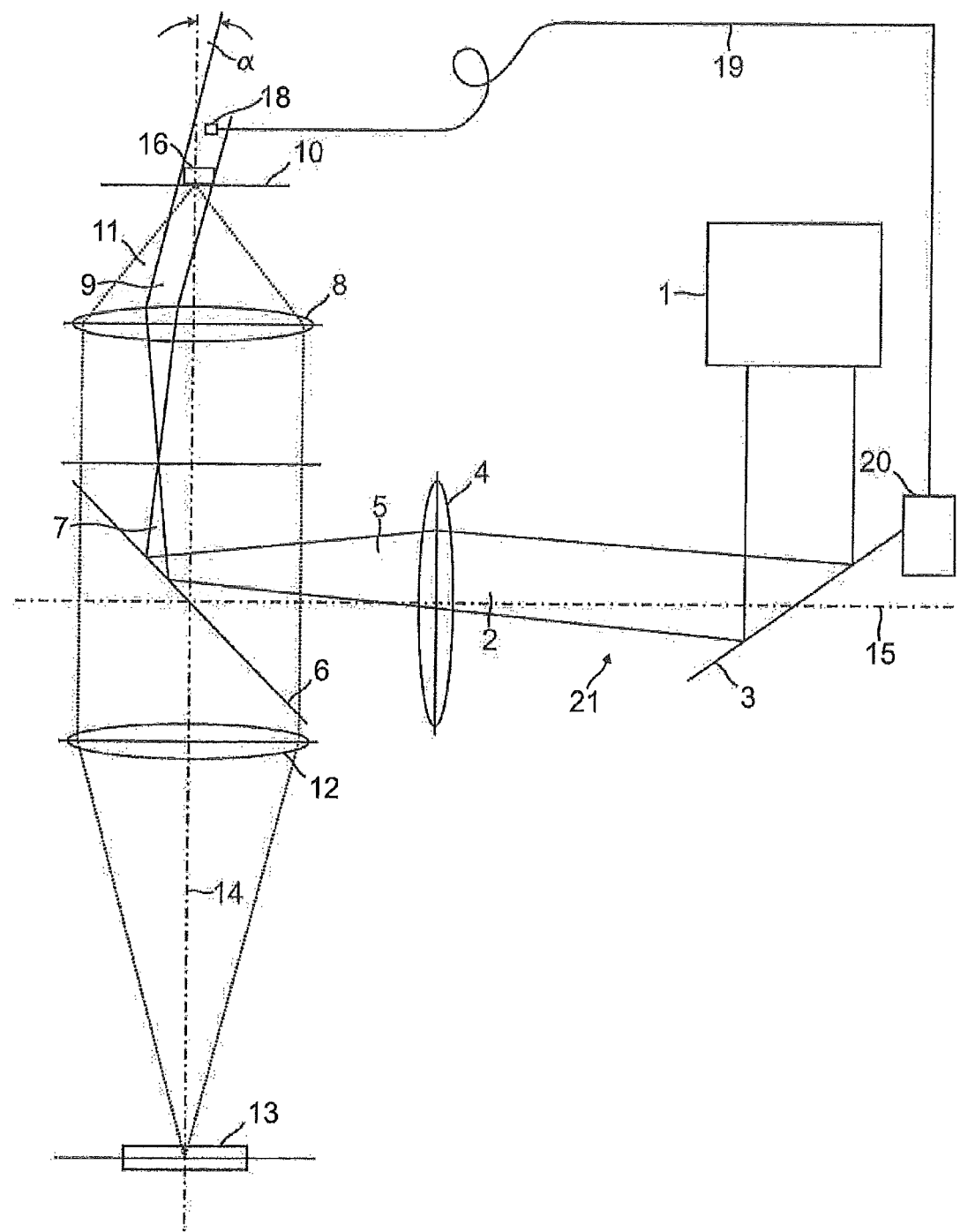
FIG. 2 schematically depicts a microscope according to the present invention with a lateral offset of the illumination light beam path relative to the optical axis of the objective.

The depiction in FIG. 2 is similar to that of FIG. 1, once again with scales deviating greatly from reality for the purpose of elucidation. The lateral offset of illumination light ray bundle 7, whose axis of symmetry extends with a lateral offset from optical objective axis 14, is elucidated here. For this purpose, illumination light beam path manipulation device 21 has received a control instruction, whereupon illumination light beam path manipulation device 21 tilts mirror 3 contained therein so that the direction of ray bundle 2 deriving from light source 1 is changed in such a way that after lens element 4 of illumination light beam path manipulation device 21, said bundle is laterally offset and convergent, as shown by ray bundle 5 emerging from the illumination light beam path manipulation device. Tilting of mirror 3 can be accomplished in two different tilt directions, i.e. within the drawing plane, and out of or into the drawing plane. With two tilt directions, any point on the objective surface can be traveled to. As an inexpensive solution, it is also possible to implement only one tilt direction, with the result that the illumination beam can be offset only along a lateral line with respect to the optical objective axis.

This lateral offset of convergent ray bundle 5 continues after reflection at mirror 6, and after passage through objective 8 causes illumination light ray bundle 9 emerging from objective 8 to be collimated and to have an angle α with respect to optical objective axis 14. This angle α is, however, negligibly small in terms of effective illumination of specimen 16. Detected light 11 is emitted from specimen 16. Here as in FIG. 1, for the purpose of clearer depiction only the light emitted from one point of specimen 16 is depicted by way of example. It is understood that in reality, multiple points of specimen 16 radiate light. This can be a mixture of the desired fluorescent light as well as light reflected and scattered from the sample. It is focused by objective 8, in conjunction with tube lens 12, onto detector 13. Because for most applications, at least for utilization in localization microscopy, what is to be detected is principally the fluorescent light emitted in all directions, and because the light reflected and scattered from the specimen is for most applications in fact blocked by a color filter, the angle at which the illumination light strikes specimen 16 can be particularly ignored, since the influence of this angle on the reflection direction does not influence evaluation if the reflected light is in any case blocked and only the fluorescent light (which is in any case emitted in all directions) is detected.

In reality illumination light ray bundle 7 penetrating into objective 8 has an even smaller cross section, in relation to the objective area, than depicted in FIG. 2; in other words, only a small percentage of the aperture or of the objective area is utilized.

Figure 3:
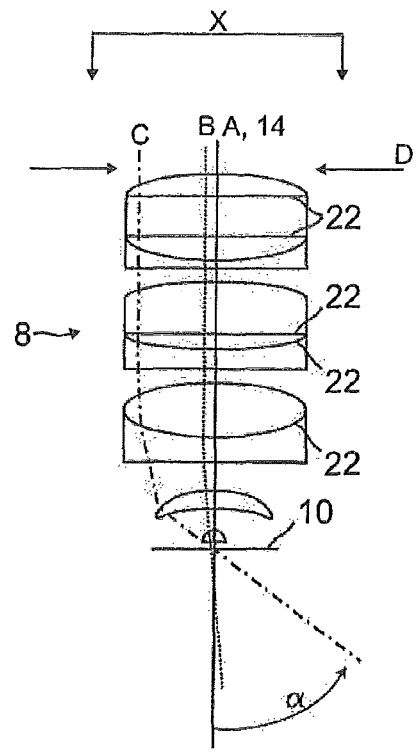
FIG. 3 is a sectioned depiction, labeled Y-Z in FIG. 4, of the objective with different illumination light beam paths A, B, C.

FIG. 3 depicts an example of an objective 8, which in FIGS. 1 and 2 was depicted for the sake of simplicity as merely a single lens element. FIG. 3 represents a schematic sectioned depiction in accordance with the section labeled Y-Z in FIG. 4. Rather than a single lens element, objectives in reality are typically made up of lens arrangements comprising multiple lens elements, which are often joined to one another at least in part with optical cement. Typical cemented surfaces are labeled in FIG. 3 with the reference character 22. As mentioned initially, these cemented surfaces 22 are particularly sensitive in terms of an excessive beam load over too long a time period.

Figure 4:
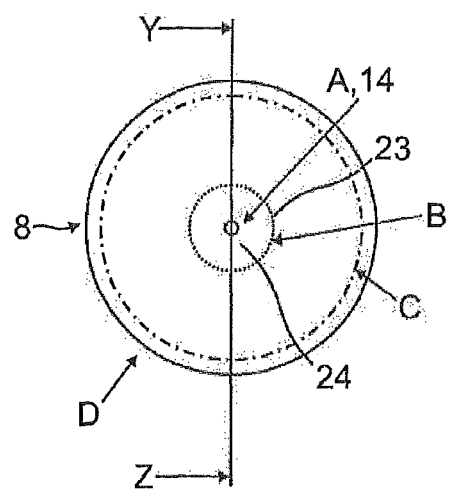
FIG. 4 is a plan view, labeled X in FIG. 3, of the objective with different illumination light beam paths A, B, C.

FIG. 3 depicts three different beam paths. A first beam path A is identical to the optical objective axis, a second beam path B is arranged with somewhat of an offset with respect to the optical objective axis, and a third beam path C has a large offset relative to optical objective axis 14. The aperture is labeled D. FIG. 4 represents a plan view of objective 8. This plan view is labeled X in FIG. 3.

It is understood that in reality, ray bundles having a specific cross section are sent along beam paths A, B, C (which are depicted in FIG. 3 only by way of their respective illumination axes) into objective 8 and are collimated by it, as has already been depicted and explained with reference to FIGS. 1 and 2. This is necessary because this is a widefield illumination system, in which the entire field being viewed is illuminated in object plane 10.

As can readily be gathered from FIG. 3, the greater the lateral offset of illumination light beam path A, B, C with respect to the optical objective axis, the greater the angle α at which the illumination light arrives at object plane 10. According to illumination beam path B, the illumination light travels out of objective 8 into object plane 10 at an exit angle deviating only very slightly from the optical axis. The illuminated sample emits light in all directions, on the one hand fluorescent light and on the other hand reflected and scattered light. For localization microscopes the fluorescent light is of particular interest; it can, for example, be filtered out of the overall detected light using a color filter before the detected beam is sent onto the location-allocating detector 13 (see FIG. 2).

As is clear from FIG. 4, however, even a small parallel offset of illumination light beam path B opens up a plurality of illumination light entry sites, specifically in the form of a circular ring 23 that extends concentrically around optical objective axis 14. It is understood that if an offset in accordance with beam path B is still permissible, smaller offsets are also permissible, since they result in smaller deviation angles α. The result is a permissible illumination light entry area 24 on objective 8, which can be predetermined and which, depending on the application, can also be modified by means of a control signal.

Figure 5:
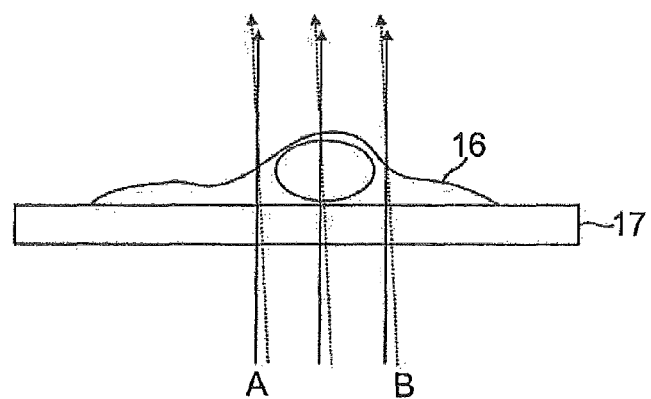
FIG. 5 is a side view of a specimen and specimen carrier with two different illumination light beam paths A and B.
Figure 6:
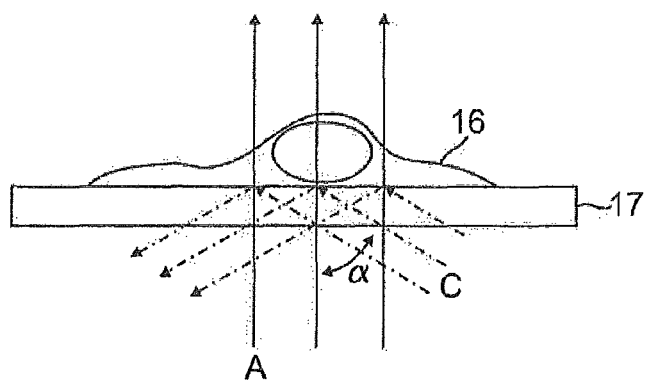
FIG. 6 is a side view of a specimen and specimen carrier with two different illumination light beam paths A and C, where illumination light beam path C demonstrates the special case of TIRF illumination.

A further particular application of the invention is depicted schematically in FIGS. 5 and 6. In this exemplifying embodiment as well, the illumination beam path extends upward from below, as is the case e.g. in an inverted microscope. Specimen 16 can be, for example, a cell that is arranged on a coverslip 17. Multiple beams in accordance with beam paths A and B, as was explained, for example, in FIGS. 3 and 4, are depicted in this drawing as well, beam path B being based on a slight offset relative to the optical objective axis. The fact that widefield illumination is involved has been taken into account in this depiction according to FIG. 5 by the fact that multiple beams in accordance with beam paths A and B are depicted, not simply the illumination axes of beam paths A, B, and C as depicted in FIG. 3. As is apparent, an angle deviating slightly from epifluorescence illumination is negligible in practice in terms of the illumination of specimen 16.

FIG. 6 depicts beam path C (likewise having multiple beams corresponding to widefield illumination) as having a large angle deviating from the optical axis, which results when there is a large offset between the illumination light entry site and the optical axis of the objective as was depicted in FIGS. 3 and 4. This special case of a large angle α can be used for so-called TIRF illumination. This type of illumination involves utilizing the effect of total reflection at the interface of the media, which in this case requires that the refractive index of specimen 16 (in this case, a cell) be less than the refractive index of the specimen carrier (in this case, the refractive index of coverslip 17). For a large angle α, total reflection then occurs at the interface between coverslip 17 and specimen 16. Illumination of specimen 16 does still occur in this case as well, however, but only in the evanescent field. This yields a further application of the invention, namely the possibility of switching over between normal illumination of the sample and TIRF illumination. This switchover requires only that a control instruction, with which the predetermined illumination light entry area is modified, be given to control system 20 (see FIG. 2). The theoretical maximum possible offset between the optical objective axis and the illumination light entry site is determined by aperture D. Because the angle α becomes larger as the offset increases, the angle α becomes smaller as the offset decreases. For TIRF illumination, however, the angle α must not fall below the respective angle at which total reflection occurs. The predetermined illumination light entry area that defines the illumination light entry sites for TIRF illumination thus turns out to be an annular area. The predetermined illumination light entry area 24 permissible for normal illumination, on the other hand, can be a circular area (see FIG. 4) that is surrounded by the annular predetermined TIRF illumination light entry area.

The illumination light entry sites are automatically modified within the predetermined illumination light entry areas permissible for the respective applications; this can occur at predefined time intervals and according to a predefined pattern, but can also occur as a function of measurement signals, for example as depicted in FIG. 2, by measuring the transmittance of objective 8 using a measurement device 18 that can deliver a signal via a signal lead 19 to a control system 20, and the illumination light entry site is modified when the transmittance drops below a specific limit value. Other criteria for modifying the illumination light entry site as a function of time can be the beam load, which is calculated as the product of beam intensity and time for the respective illumination light entry site. The entry sites can also be modified over time using a random generator that is a constituent of control system 20.

PARTS LIST

1 Light source
2 Ray bundle
3 Mirror
4 Lens element
5 Ray bundle (emerging from illumination light beam path manipulation device)
6 Dichroic mirror
7 Ray bundle (converging, reflected from dichroic mirror)
8 Objective
9 Ray bundle (emerging from objective as collimated illumination light)
10 Object plane
11 Detected light
12 Tube lens
13 Detector
14 Optical objective axis
15 Additional axis of symmetry 16 Specimen
17 Coverslip
18 Measurement device
19 Signal lead
20 Control system
21 Illumination light beam path manipulation device
22 Cemented surfaces
23 Circular ring
24 Permissible illumination light entry area

What is claimed is:

1. A widefield microscope illumination system, wherein:
the widefield microscope illumination system is adapted to be used for a localization microscope and further comprises;
a microscope objective that comprises an optical objective axis;
an illumination light source that sends widefield illumination light along illumination beam paths having corresponding illumination axes along which the illumination light penetrates into the microscope objective through illumination light entry sites located within a predetermined illumination light entry area of the objective; wherein an illumination beam cross section at the illumination light entry sites is smaller than the overall predetermined illumination light entry area of the objective;
a spatially resolving light detector that detects detected light sent from an illuminated sample through the microscope objective along a detected light beam path; and
an automatic illumination light beam path manipulation device, controlled by a control system, which is arranged in front of the microscope objective in relation to the direction of the illumination light beam path, and by means of which illumination light beam path manipulation device the illumination axes are automatically movable at time intervals to a plurality of different illumination light entry sites within the predetermined illumination light entry area.

2. The widefield microscope illumination system according to claim 1, wherein the illumination axes always extend parallel to the objective axis.

3. The microscope illumination system according to claim 1, wherein the illumination light beam path manipulation device comprises an optomechanical system, acousto-optical modulators (AOMs), or electro-optical modulators (EOMs), which establish an adjustable beam offset and thus an illumination light entry site that is adjustable with respect to the optical objective axis.

4. The microscope illumination system according to claim 1, wherein the control system is configured in such a way that it automatically controls, according to a predefined pattern, a permitted adjustable beam offset in the region of the predetermined illumination light entry area for the illumination light into the objective, all the illumination light entry sites permitted by the control system being located within this predetermined illumination light entry area.

5. The microscope illumination system according to claim 1, wherein the control system comprises a random generator that controls a permitted adjustable beam offset in the region of the predetermined illumination light entry area for the illumination light into the objective, all the illumination light entry sites permitted by the control system being located within this predetermined illumination light entry area.

6. The microscope illumination system according to claim 1, wherein a control interface by means of which a control instruction adjusting the predetermined illumination light entry area can be entered.

7. The microscope illumination system according to claim 1, wherein the predetermined illumination light entry area is a circular, circular-segment-shaped, annular, or annular-segment-shaped area.

8. The microscope illumination system according to claim 1, wherein a measurement device that monitors the transmittance of the objective and sends a control signal to the control system when the transmittance falls below a predetermined threshold value.

9. A widefield illumination method for illuminating samples viewed with a microscope, the microscope comprising:
a microscope objective that comprises an optical objective axis; and
an illumination light source that sends widefield illumination light along illumination beam paths having corresponding illumination axes along which the illumination light penetrates into the microscope objective through illumination light entry sites located within a predetermined illumination light entry area of the objective; the method comprising:
using the widefield microscope illumination system for a localization microscope;
utilizing an illumination beam cross section at the illumination light entry sites that is smaller than the overall predetermined illumination light entry area of the objective; and
repeated, automatic, parallel adjustment of the illumination axis relative to the optical objective axis at time intervals, such that a lateral offset of the illumination axis relative to the objective axis is automatically adjusted, so that the illumination light entry site is adjusted within the predetermined illumination light entry area at time intervals such that the objective is protected from damage by illumination light.

10. The illumination method according to claim 9, wherein a parallel orientation of the illumination axes relative to the objective axis, and by maintenance of that parallelism upon automatic adjustment of the lateral offset of the illumination axis relative to the objective axis.

11. The illumination method according to claim 9, wherein a random selection of the respective illumination light entry sites of the illumination light within the predefined illumination light entry area, and by maintenance of those respective illumination light entry sites over the respective time intervals until the respective next illumination light entry site within the predefined illumination light entry sites is randomly selected.

12. The illumination method according to claim 9, wherein selection of the respective illumination light entry sites of the illumination light within the predefined illumination light entry area according to a predefined pattern, and by maintenance of those respective illumination light entry sites over the respective time intervals until the respective next illumination light entry site is selected within the predefined illumination light entry sites according to the predefined pattern.

13. The illumination method according to claim 9, wherein a measurement of the optical transmittance of the objective for the respective illumination light entry sites, and adjustment of the time intervals in accordance with a change over time in optical transmittance for the respective illumination light entry site.

* * * * *